United States Patent [19]

Jansen et al.

[11] Patent Number: 4,902,500
[45] Date of Patent: Feb. 20, 1990

[54] STABILIZATION OF ANTIBODIES

[75] Inventors: Theodorus Jansen, Venray; Engelbertus J. M. Janssen, ZL Groesbeek; Lammert Cornelius, KP Boxmeer, all of Netherlands

[73] Assignee: Akzo N.V., Arnhem, Netherlands

[21] Appl. No.: 275,250

[22] Filed: Nov. 23, 1988

[30] Foreign Application Priority Data

Nov. 27, 1987 [NL] Netherlands ................ 8702848

[51] Int. Cl.⁴ ............... A61K 31/74; A61K 31/745; A61K 39/00; A61K 39/12
[52] U.S. Cl. ............................. 424/78; 424/83; 424/88; 424/89; 424/85.1; 424/85.8; 424/92

[58] Field of Search .............. 424/88, 89, 92, 78, 424/85.1, 83, 85.8

[56] References Cited

U.S. PATENT DOCUMENTS 4,397,870 8/1983 Sloviter ........................ 514/832
4,606,918 8/1986 Allison et al. ................. 424/92

Primary Examiner—Joseph L. Schofer
Assistant Examiner—Carmen B. Pili-Curtis
Attorney, Agent, or Firm—William M. Blackstone

[57] ABSTRACT

According to the present invention antibody preparations are more stable during storage if in addition they contain a mixture of at least one polyoxypropylene-polyoxyethylene block polymer (such as Pluronic F68) and at least one phospholipid (such as lecithin).

11 Claims, No Drawings

STABILIZATION OF ANTIBODIES

This application relates to a stable aqueous solution of antibodies.

To an increasing extent, antibodies are being used in human and in veterinary medicine both for prophylactic and for diagnostic and therapeutic purposes. The antibodies used in this manner are at present primarily monoclonal antibodies which can be obtained with high purity from a culture of immortalized B-lymphocytes.

Important fields of application for antibodies are, inter alia, the prevention or cure of infectious diseases (for which, for example, antiviral, antibacterial or antiparasitic antibodies are administered) the regulation of hormone levels (in particular, of gonadotropins, for which anti-gonadotropins are administered) and the localization and/or combating of tumours (for which antibodies, optionally bonded to a labelling substance or therapeutic agent, directed against specific tumour antigens are administered).

In all these applications, the problem is to keep the aqueous solution of the antibodies stable for a sufficiently long time, not only with respect to the activity but, in particular, also with respect to the physical state of the antibody molecules. This physical instability of antibody solutions often results in aggregation formation and, in the long term, in sedimentation of the antibodies. As a result of this, constant quality of the product cannot be guaranteed, which is unacceptable for pharmaceutical products.

It has now been found that aqueous solutions of antibodies are physically stable for a sufficiently long time if they also contain a combination of a polyoxypropylene-polyoxyethylene block polymer (POP-POE block polymer) and a phospholipid.

No aggregation of the antibodies occurs in such a composition so that the solution remains clear and homogeneous while the activity of the peptide also remains intact.

The POP-POE block polymers, also termed poloxamers, are marketed under trade names such as Pluronic®, Synperonic®, Superonic® and Emkalyx®. These are compounds which consist of blocks of polyoxypropylene (POP)

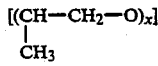

and polyoxyethylene (POE) $[(CH_2-CH_2-O)_y]$ (wherein x and y are integers) which respectively form the hydrophobic and hydrophilic components of such block polymers. Known block polymer compounds are of the normal three-block type:

HO—[POE]—[POP]—[POE]—H which include the Pluronics L31, L81, L92, L101, L131, L122, P103, F68 and F108, or of the reverse three-block type:

HO—[POP]—[POE]—[POP]—H which include the Pluronics 25R1 and 31R1, or of the normal eight-block type:

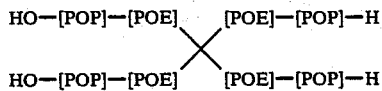

which include the Pluronics T1101, T1301 and T1501, or of the reverse eight-block type:

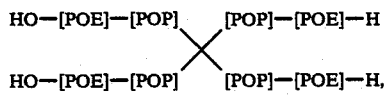

represented by, inter alia, the Pluronics T90R1, T110R1, T130R1, T130R2, T150R1, T150R4 and T150R8.

The difference between these four types stems from the differences in average chain length of the respective POP and POE blocks.

In general, use is preferably made of POP-POE three-block polymers having a mean molecular weight between approximately 950 and 4,000 and having a polyoxy-ethylene content of up to approximately 80%. Within the scope of the present invention, the most suitable representatives have, in view of their water solubility, a POE content of greater than 50%, such as, for example, Pluronic F68.

The phospholipids are esters of phosphoric acid and occur, inter alia, in lecithin. The quantitative composition of lecithin varies depending on the source. The phospholipids in lecithin comprise tens of compounds, of which the most important are phosphatidyl choline, phosphatidyl ethanolamine and phosphatidyl inositol. In addition, phosphatidyl serine, diphosphatidyl glycerol, sphingomyelin, phosphatidic acid and lysophospholipids. These components can be obtained in more or less pure form from lecithin, but if desired, they can also be prepared synthetically. According to the present invention, the aqueous solution may contain, for example, lecithin, or a fraction thereof, or a component thereof or a mixture of two or more of these components. Advantageously, use can be made of a mixture which consists mainly of phosphatidyl choline and phosphatidyl ethanolamine (preferably, at least approximately 90%) and small quantities of phosphatidyl inositol and lysophospholipids.

The quantity of block polymer in the solution according to the invention is preferably between 0.01 and 5%, the quantity of phospholipids preferably between 0.0001 and 1%, and the concentration of antibodies is preferably between 0.001 and 1 mg/ml.

The antibodies which can be stabilized according to the present invention may, for example, consist of, or be obtained from, antiserum (polyclonal antibodies) or be produced by immortalized B-lymphocytes (monoclonal antibodies), or possibly by triomas or quadromas (which produce bivalent monoclonal antibodies) or by preferably eukaryotic host cells which have been transformed with recombinant DNA, at least a part of which codes for a (possibly chimaeric) antibody or an antigen-bonding fragment thereof.

The relevant antibodies may be directed against any antigen or hapten of, for example, diagnostic, prognostic, therapeutic or prophylactic importance. Suitable antigens are, for example, directed against hormones and, in particular, against gonadotropic hormones such as human chorionic gonadotropin, follicle-stimulating hormone, lutenizing hormone, "pregnant mare serum gonadotropin" (PMSG), and human menopausal gonadotropin.

In livestock breeding, PMSG is used to promote pregnancy, and specifically, the number of offspring. Antibodies for PMSG (anti-PMSG) are then administered after some time to eliminate the disadvantageous effects of a high PMSG content in the blood for the fertilized egg cell.

The invention is explained by reference to the following examples.

EXAMPLE 1

| | | |
|---|---|---|
| Monoclonal anti-PMSG | (R) | 880 μg |
| Phospholipid mixture (Infusol) | | 10 μg |
| Pluronic F68 | | 3 mg |
| Glycine | | 7.06 mg |
| Benzyl alcohol | | 10 mg |
| Water for injection to make | | 1 ml |

EXAMPLE 2

| | | |
|---|---|---|
| Monoclonal anti-PMSG | (R) | 200 μg |
| Phospholipid mixture (Infusol) | | 10 μg |
| Pluronic F68 | | 6 mg |
| Glycine | | 7.06 mg |
| Benzyl alcohol | | 10 mg |
| Water for injection to make | | 1 ml |

EXAMPLE 3

| | |
|---|---|
| Monoclonal anti-HCG | 0.75 mg |
| Phospholipon 100 | 100 μg |
| Pluronic F87 | 1 mg |
| Phosphate buffer, 0.07 M, pH = 8 | 0.9 ml |
| Water for injection to make | 1 ml |

EXAMPLE 4

| | |
|---|---|
| Monoclonal anti-K99 | 0.85 mg |
| Phospholipon 100 | 100 μg |
| Pluronic F38 | 1 mg |
| Thiomersal | 0.1 mg |
| Glucose | 100 mg |
| Phosphate buffer, 0.05 M, pH = 7 | 0.8 ml |
| Purified water to make | 1 ml |

EXAMPLE 5

| | | |
|---|---|---|
| Monoclonal anti-PST (porcine somatotropin) | | 3.0 mg |
| Epicuron 125 | | 0.5 mg |
| Pluronic L121 | | 10 mg |
| Carbonate buffer 0.05 M pH = 8.5 | | 0.6 ml |
| Water for injection | ad | 1 ml |

EXAMPLE 6

| | | |
|---|---|---|
| Monoclonal anti-GnRH | | 2.5 mg |
| Infusol | | 50 μg |
| Pluronic F38 | | 1 mg |
| Glycocol | | 7.5 mg |
| Benzylalcohol | | 10 mg |
| Water for injection | ad | 1 ml |

EXAMPLE 7

| | | |
|---|---|---|
| Monoclonal anti-inhibin | | 1.0 mg |
| Lecithin | | 10 mg |
| Pluronic L121 | | 50 mg |
| Phosphate buffer pH = 6 | | 0.6 ml |
| Methylparaten | | 1.0 mg |
| Water for injection | ad | 1 ml |

The stability and activity of the antibody solutions described in Examples 1 and 2 have been studied for many months. At the same time, they were compared with solutions which contained no POP-POE block polymer and phospholipid. The results are shown in the table below:

| | \multicolumn{15}{c}{Preparation No.} | | | | | | | | | | | | | | |
|---|---|---|---|---|---|---|---|---|---|---|---|---|---|---|---|
| | 7900 Monoclonal 167 μg/ml; benzyl alcohol; 1% glycine buffer | | | 8285 Monoclonal 167 μg/ml; gelatin A 0.1%; benzyl alcohol 1%; glycine buffer | | | 8488 (Example 1) Monoclonal 880 μg/ml; Infusol 0.001%; Pluronic F68 0.3%; benzyl alcohol 1%; glycine buffer | | | 8984 (Example 2) Monoclonal 200 μg/ml; Infusol 0.001%; Pluronic F68 0.6%; benzyl alcohol 1%; glycine buffer | | | 9566 Monoclonal 200 μg/ml; Infusol 0.001%; Pluronic F68 0.3%; benzyl alcohol 1%; glycine buffer | | |
| | 4° C. | 25° C. | 37° C. | 4° C. | 25° C. | 37° C. | 4° C. | 25° C. | 37° C. | 4° C. | 25° C. | 37° C. | 4° C. | 25° C. | 37° C. |
| Physical stability | | | | | | | | | | | | | | | |
| T₀ | + | | | + | | | + | | | + | | | + | | |
| 1 week | + | + | − | + | + | ± | ± | + | + | | | | | | |
| 2 weeks | + | + | − | + | ± | − | + | + | + | + | + | + | + | + | + |
| 1 month | + | + | − | + | ± | − | | | | + | + | + | + | + | + |
| 2 months | ± | − | − | + | − | − | | | | + | ± | + | | | |
| 3 months | | | | ± | | | + | + | + | + | + | + | + | + | + |
| 6 months | | | | − | | | ± | − | − | + | + | ± | + | + | + |
| 9 months | | | | + | − | − | ± | ± | − | | | | | | |
| 12 months | | | | − | | | | | | + | + | ± | + | + | + |
| 18 months | | | | − | | | | | | + | + | + | | | |
| Activity IU/ml | | | | | | | | | | | | | | | |
| T₀ | | | | − | | | | | | 1410 | | | 1368 | | |
| 1 week | | | | 1040 | 1030 | 1020 | | | | | | | | | |
| 2 weeks | | | | 980 | 940 | 700 | | | | | | | 1296 | 1230 | 1164 |

-continued

| | Preparation No. | | | | | | | | | | | | | | |
|---|---|---|---|---|---|---|---|---|---|---|---|---|---|---|---|
| | 7900 Monoclonal 167 µg/ml; benzyl alcohol; 1% glycine buffer | | | 8285 Monoclonal 167 µg/ml; gelatin A 0.1%; benzyl alcohol 1%; glycine buffer | | | 8488 (Example 1) Monoclonal 880 µg/ml; Infusol 0.001%; Pluronic F68 0.3%; benzyl alcohol 1%; glycine buffer | | | 8984 (Example 2) Monoclonal 200 µg/ml; Infusol 0.001%; Pluronic F68 0.6%; benzyl alcohol 1%; glycine buffer | | | 9566 Monoclonal 200 µg/ml; Infusol 0.001%; Pluronic F68 0.3%; benzyl alcohol 1%; glycine buffer | | |
| 1 month | | | | 1040 | 1010 | 940 | | | | 1130 | 960 | 1040 | 1248 | 1152 | 1080 |
| 2 months | | | | 1000 | 1000 | 940 | 6400 | 6400 | 6000 | 1300 | 1160 | 940 | | | |
| 3 months | | | | 1040 | 990 | 910 | 5040 | 5400 | 5400 | 1320 | 1296 | 1128 | 1188 | 1080 | 912 |
| 6 months | | | | | | | 6600 | 6060 | 4440 | 1512 | 1248 | 360 | 1440 | 1044 | 486 |
| 9 months | | | | | | | | | | | | | | | |
| 12 months | | | | | | | | | | 1296 | 1128 | 264 | 1212 | 972 | 392 |
| 18 months | | | | | | | | | | 1272 | 876 | 252 | | | |

I claim:

1. Stable aqueous solution of antibodies, comprising antibodies and at least one polyoxypropylene-polyoxyethylene block polymer and at least one phospholipid in amounts effective to prevent the formation of antibody aggregates or antibody sedimentation.

2. Aqueous solution according to claim 1, wherein the polyoxypropylene-polyoxyethylene block polymer has a molecular weight between about 950 and about 4,000 daltons.

3. Aqueous solution according to claim 1 wherein the polyoxypropylene-polyoxyethylene block polymer has a polyoxyethylene content of no more than 80%.

4. Aqueous solution according to claim 3, wherein the polyoxypropylene-polyoxyethylene block polymer has a polyoxyethylene content of at least 50%.

5. Aqueous solution according to claim 1, comprising lecithin as a phospholipid.

6. Aqueous solution according to claim 1, comprising 0.01–5% by weight polyoxypropylene-polyoxyethylene block polymer.

7. Aqueous solution according to claim 1, comprising 0.0001–1% by weight phospholipid.

8. Aqueous solution according to claim 1, comprising 0.001–1 mg of antibody/ml.

9. Aqueous solution according to claim 6, comprising 0.0001–1% by weight phospholipid.

10. Aqueous solution according to claim 9, comprising 0.001–1 mg of antibody/ml.

11. A method for stabilizing aqueous solutions of antibodies, comprising mixing with the solution at least one polyoxypropylene-polyoxyethylene block polymer in an amount to achieve concentration of 0.01–5% by weight polyoxypropylene-polyoxyethylene block polymer and at least one phospholipid in an amount to achieve a concentration of 0.001–1% by weight phospholipid, whereby the formation of antibody aggregates and the sedimentation of antibodies is prevented.

* * * * *